US005922681A

United States Patent [19]
Doherty et al.

[11] Patent Number: 5,922,681
[45] Date of Patent: Jul. 13, 1999

[54] ENDOTHELIN ANTAGONISTS

[75] Inventors: Annette Marian Doherty, Ann Arbor, Mich.; David Charles Rees, Cambridge, United Kingdom

[73] Assignee: Warner-Lambert Company, Morris Plains, N.J.

[21] Appl. No.: 07/945,316

[22] Filed: Sep. 14, 1992

[51] Int. Cl.$^6$ ....................................................... C07K 5/06
[52] U.S. Cl. ............................ 514/19; 562/445; 562/433
[58] Field of Search .............................. 514/19; 562/433, 562/445

[56] References Cited

FOREIGN PATENT DOCUMENTS

| 0436189 | 12/1990 | European Pat. Off. . |
| 0405537 | 2/1991 | European Pat. Off. ...... C07D 209/20 |
| 0457195 | 5/1991 | European Pat. Off. . |

OTHER PUBLICATIONS

*Nature* 344:114 (1990), Watanabe et al., "Endothelin in Myocardial Infarction".
*Circulation* 82:2226 (1990) Margulies et al., "Increased Endothelin in Experimental Heart Failure".
*J. Clin. Invest.* 83:1762 (1989) Kon et al., "Glomerular Actions of Endothelin In Vivo".
*J. Am. Soc. Nephrol.* 1:76 (1990) Perico et al., "Endothelin Mediates the Renal Vasoconstriction . . . ".
*Chem. Pharm. Bull.* 39:1295 (1991) Koshi et al., "Inhibition of Endothelin (ET)–1 and ET–2 . . . ".
*Clin. Exp. Pharmacol. Physiol.* 17:691 (1990), Miyamori et al., "Systemic and Regional Effects . . . ".
*J. Tokyo Women's Med. Coll.* 61:951 (1991) Ohno, "Effects of Endothelin–Specific Antibodies . . . ".
*Circulation* 83:1808 (1991) Lerman et al., "Endothelin has Biological Actions at Pathophysiological . . . ".
*Am. J. Physiol.* 259:F312 (1990), Cavero et al., "Endothelin in Experimental Congestive Heart . . . ".
*Am. J. Hypertension* 4:9A (1991) Rodeheffer et al., "Circulating Plasma Endothelin Correlates with . . . ".
*Hypertension* 15:729 (1990) Mortenson et al., "Chronic Hypertension Produced by Infusion . . . ".
*Nature* 348:730 (1990) Arai et al.
*Nature* 348:732 (1990), Sakurai et al.
*Proc. Natl. Acad. Sci.* 88:3185 (1991) Lin et al.
*Biochem. Biophys. Res. Chem.* 178:656 (1991) Sakamato et al.
*FEBS Lett.* 287:23 (1991) Hosoda et al.
*FEBS Lett.* 282:103 (1991) Takayanagi et al.
*Biochem. Biophys. Res. Commun.* 183(2):566 (1992) Panek et al.
*Biochem. Biophys. Res. Commun.* 175:556 (1991) Williams et al.
*Biochem. Biophys. Res. Commun.* 179:286 (1991) Saeki et al.
*British Journal of Pharmacology* 101:232–236 (1990), Rovero et al.
*J. Cardiovasc. Pharm.* 17 (supp. 7):S59–S61 (1991) Doherty et al.
*Proc. Natl.Acad. Sci.* USA 88:7443 (1991) Spinella et al.
*FASEB J.* 6:A1005 (1992) Werber et al., "DPR–1 ASP–15 Endothelin–1 does not Antagonize Endothelin . . . ".
*J. Med. Chem.* 35:3301 (1992) Cody et al., "Design of a Functional Hexapeptide Antagonist . . . ".
*FASEB J.* 6 (Part 1, No. 4):392 (1992) Hingorani et al. "In Vitro Pharmacology of a Non Selective . . . ".
*FASEB J.* 6 (part 1, No. 4):390 (1992) LaDouceur et al. "Effects of the endothelin receptor antagonist . . . ".
*Biochem. Biophys. Res. Commun.* 178:132 (1991), Ihara et al., "An Endothelin Receptor ($ET_A$) Antagonist . . . ".
*J. Med. Chem.* 35:2139 (1992) Ishikawa et al., "Cyclic Pentapeptide Endothelin Antagonists . . . ".
*Life Sci.* 50:247 (1992) Ihara et al.
*J. Med. Chem.* 34:404–414 (1991).

*Primary Examiner*—Cecilia J. Tsang
*Assistant Examiner*—David Lukton
*Attorney, Agent, or Firm*—Elizabeth M. Anderson

[57] ABSTRACT

Antagonists of endothelin are described, as well as methods of using them and pharmaceutical compositions containing them. These compounds are useful in controlling hypertension, myocardial infarction, pulmonary hypertension, angina, metabolic, endocrinological, and neurological disorders, congestive heart failure, septic or endotoxic shock, subarachnoid hemorrhage, arrhythmias, asthma, acute and chronic renal failure, preeclampsia, and diabetes.

16 Claims, No Drawings

ENDOTHELIN ANTAGONISTS

BACKGROUND OF THE INVENTION

The present invention relates to certain modified amino acids and modified dipeptides which have now been found to possess endothelin receptor antagonistic activity. The compounds of the invention will be useful in cardiovascular diseases, especially in controlling hypertension, myocardial ischemia, congestive heart failure, arrhythmias, pulmonary hypertension, and angina. They will also be useful in renal diseases, including acute and chronic renal failure. They will be useful in vascular disorders such as: atherosclerosis, Buergers disease, Takayasu's arteritis, and Raynaud's phenomenon. They will be useful in cancer, especially pulmonary carcinoma; in endocrine disorders; in preeclampsia; in metabolic disorders such as diabetes; in neurological disorders especially subarachnoid hemorrhage; in various gastrointestinal diseases; in septic or endotoxic shock; and in bronchopulmonary diseases, especially asthma.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs). The unique bicyclic structure and corresponding arrangement of the disulfide bridges of ET-1, which are the same for the endothelins, VIC, and the sarafotoxins, has led to significant speculation as to the importance of the resulting induced secondary structure to receptor binding and functional activity. ET-1 analogues with incorrect disulfide pairings exhibit at least 100-fold less vasoconstrictor activity.

Endothelin is involved in many human disease states.

Several in vivo studies with ET antibodies have been reported in disease models. Left coronary artery ligation and reperfusion to induce myocardial infarction in the rat heart, caused a four- to sevenfold increase in endogenous endothelin levels. Administration of ET antibody was reported to reduce the size of the infarction in a dose-dependent manner (Watanabe, T., et al, "Endothelin in Myocardial Infarction," *Nature* (Lond.) 344:114 (1990)). Thus, ET may be involved in the pathogenesis of congestive heart failure and myocardial ischemia (Margulies, K. B., et al, "Increased Endothelin in Experimental Heart Failure," *Circulation* 82:2226 (1990)).

Studies by Kon and colleagues using anti-ET antibodies in an ischemic kidney model, to deactivate endogenous ET, indicated the peptide's involvement in acute renal ischemic injury (Kon, V., et al, "Glomerular Actions of Endothelin In Vivo," *J. Clin. Invest.* 83:1762 (1989)). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico, N., et al, "Endothelin Mediates the Renal Vasoconstriction Induced by Cyclosporine in the Rat," *J. Am. Soc. Nephrol.* 1:76 (1990)).

Others have reported inhibition of ET-1 or ET-2-induced vasoconstriction in rat isolated thoracic aorta using a monoclonal antibody to ET-1 (Koshi, T., et al, "Inhibition of Endothelin (ET)-1 and ET-2-Induced Vasoconstriction by Anti-ET-1 Monoclonal Antibody," *Chem. Pharm. Bull.,* 39:1295 (1991)).

Combined administration of ET-1 and ET-1 antibody to rabbits showed significant inhibition of the BP and renal blood flow responses (Miyamori, I., et al, Systemic and Regional Effects of Endothelin in Rabbits: Effects of Endothelin Antibody. *Clin. Exp. Pharmacol. Physiol.,* 17:691 (1990)).

Other investigators have reported that infusion of ET-specific antibodies into SHR decreased MAP, and increased glomerular filtration rate and renal blood flow. In the control study with WKY there were no significant changes in these parameters (Ohno, A. Effects of Endothelin-Specific Antibodies and Endothelin in Spontaneously Hypertensive Rats. *J. Tokyo Women's Med. Coll.,* 61:951 (1991)).

Elevated levels of endothelin have been reported in several disease states (see Table II below).

Burnett and co-workers recently demonstrated that exogenous infusion of ET (2.5 ng/kg/mL) to anesthetized dogs, producing a doubling of the circulating concentration, did have biological actions (Lerman, A., et al, "Endothelin has Biological Actions at Pathophysiological Concentrations," *Circulation* 83:1808 (1991)). Thus heart rate and cardiac output decreased in association with increased renal and systemic vascular resistances and antinatriuresis. These studies support a role for endothelin in the regulation of cardiovascular, renal, and endocrine function.

In the anesthetized dog with congestive heart failure, a significant two- to threefold elevation of circulating ET levels has been reported (Cavero, P. G., et al, "Endothelin in Experimental Congestive Heart Failure in the Anesthetized Dog," *Am. J. Physiol.* 259:F312 (1990)), and studies in humans have shown similar increases (Rodeheffer, R. J., et al, "Circulating Plasma Endothelin Correlates With the Severity of Congestive Heart Failure in Humans," *Am. J. Hypertension* 4:9A (1991)). When ET was chronically infused into male rats, to determine whether a long-term increase in circulating ET levels would cause a sustained elevation in mean arterial blood pressure, significant, sustained, and dose-dependent increases in mean arterial BP were observed. Similar results were observed with ET-3 although larger doses were required (Mortenson, L. H., et al, "Chronic Hypertension Produced by Infusion of Endothelin in Rats," *Hypertension,* 15:729 (1990)).

The distribution of the two cloned receptor subtypes, termed $ET_A$ and $ET_B$, have been studied extensively (Arai, H., et al, *Nature* 348:730 (1990), Sakurai, T., et al, *Nature* 348:732 (1990)). The $ET_A$, or vascular smooth muscle receptor, is widely distributed in cardiovascular tissues and in certain regions of the brain (Lin, H. Y., et al, *Proc. Natl. Acad. Sci.* 88:3185 (1991)). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto, A., et al, *Biochem. Biophys. Res. Chem.* 178:656 (1991), Hosoda, K., et al, *FEBS Lett.* 287:23 (1991)). The $ET_A$ receptor clearly mediates vasoconstriction and there have been a few reports implicating the $ET_B$ receptor in the initial vasodilatory response to ET (Takayanagi, R., et al, *FEBS Lett.* 282:103 (1991)). However, recent data has shown that the $ET_B$ receptor mediates vasoconstriction in some tissue beds (Panek, R. L., et al, *Biochem. Biophys. Res. Commun.* 183 (2):566 (1992).

Comparison of the receptor affinities of the ET's and SRTX's in rats and atria ($ET_A$) or cerebellum and hippocampus (ET$_B$), indicate that SRTX-c is a selective ET$_B$ ligand (Table 1) (Williams, D. L., et al, *Biochem. Biophys. Res. Commun.*, 175:556 (1991)). A recent study showed that selective ET$_B$ agonists caused only vasodilation in the rat aortic ring, possibly through the release of EDRF from the endothelium (ibid). Thus, reported selective ET$_B$ agonists, for example, the linear analog ET[1,3,11,15-Ala] and truncated analogs ET[6-21, 1,3,11,15-Ala], ET[8-21,11,15-Ala], and N-acetyl-ET[10-21] caused vasorelaxation in isolated, endothelium-intact porcine pulmonary arteries (Saeki, T., et al, *Biochem. Biophys. Res. Commun.* 179:286 (1991)). However, some ET analogs are potent vasoconstrictors in the rabbit pulmonary artery, a tissue that appears to possess an ET$_B$, nonselective type of receptor (ibid).

The flexible C-terminal hexapeptide of ET-1 has been shown to be important for binding to the ET receptor and functional activity in selected tissues. Additionally, the C-terminal amino acid (Trp-21) has a critical role in binding and vasoconstrictor activity, since ET[1-20] exhibits approximately 1000-fold less functional activity.

Rovero, P., et al, *British Journal of Pharmacology* 101:232–236 (1990) disclosed various analogs of the C-terminal hexapeptide of ET-1, none of which exhibited functional activity against the vasoconstrictor effects of ET-1.

Doherty, et al, in *J. Cardiovasc. Pharm.* 17 (Suppl. 7):S59–S61, 1991) disclosed various analogues of the C-terminal hexapeptide of ET-1, none of which exhibited any functional activity against the vasoconstrictor effects of ET-1.

A full length ET analogue, ET-1[Dpr1-Asp15] (where Dpr=diaminopropionic acid), has been reported as a specific ET$_A$ antagonist by Spinella and co-workers (Spinella, M. J., et al, "Design and Synthesis of a Specific Endothelin 1 Antagonist: Effects on Pulmonary Vasoconstriction," *Proc. Natl. Acad. Sci.* USA, 88:7443 (1991); Werber, A. W., et al, "DPR-1 ASP-15 Endothelin-1 does not Antagonize Endothelin-1 in the Superior Cerebellar Artery of Rats," *FASEB J.*, 6:A1005 (1992)).

SAR studies around the D-Phe$^{16}$ position with different aromatic substitutions have led to the potent functional ET$_A$/ET$_B$ antagonist (Cody, W. C., et al, "Design of a Functional Hexapeptide Antagonist of Endothelin," *J. Med. Chem.*, 35:3301 (1992)); Hingorani, G., et al, In Vitro Pharmacology of a Non-Selective ET$_A$/ET$_B$ endothelin receptor antagonist, PD 142893 (Ac-(β-phenyl)D-Phe-L-Leu-L-Asp-L-lle-L-lle-L-Trp trifluoroacetate). *FASEB J.*, 6 (Part 1, No. 4):392 (1992); LaDouceur, D. M., et al, Effects of the endothelin receptor antagonist PD 142893 (Ac-(β-phenyl)D-Phe-L-Leu-L-Asp-L-lle-L-lle-L-Trp Trifluoroacetate) on endothelin-1 (ET-1) Induced Vasodilation and Vasoconstrictor in Reguional Arterial Beds of the Anesthetized Rat. *FASEB J.*, 6(Part 1, No. 4):390 (1992)). This displays moderate binding selectivity (tenfold) for the ET$_A$ receptor over the ET$_B$ subtype. Moveover, it is a functional antagonist of endothelin-induced arachidonic acid release in vascular smooth muscle cells (ET$_A$) and antagonizes endothelin-stimulated constriction in the rabbit femoral renal (ET$_A$), and pulmonary arteries (ET$_B$). A report of a cyclic pentapeptide ET$_A$ receptor antagonist discovered by random screening of fermentation products from *Streptomyces misakiensis* has recently appeared (Ihara, M., et al, "An Endothelin Receptor (ET$_A$) Antagonist Isolated from Streptomyces Misakiensis," *Biochem. Biophys. Res. Commun.* 178:132 (1991); Ishikawa, K., et al, "Cyclic Pentapeptide Endothelin Antagonists With High ET$_A$ Selectivity. Potency and Solubility Enhancing Modifications," *J. Med. Chem.* 35:2139 (1992); Kiyofumi, I., et al, "EPA 0 436 189 A1; Endothelin Antagonistic Cyclic Pentapeptides," Filed Dec. 20, 1990). Structure-activity studies around this peptide BE-18257B cyclo[D-Trp-D-Glu-Ala-D-allo-lle-Leu]) have led to more potent analogs BQ-123 and BQ-153. Both BQ-123 and BQ-153 antagonize ET-1-induced vasoconstriction of isolated porcine coronary arteries (Ishikawa, K., et al, op.cit.), Kiyofumi, I., et al, op.cit.), (Ihara, M., et al, *Life Sci.* 50:247 (1992). There was a small amount of ET-1-induced vasoconstriction resistant to these antagonists presumably mediated by the ET$_B$ receptor subtype. In conscious rats, pretreatment with these antagonists antagonized ET-1-induced sustained pressor responses dose dependently without affecting depressor action of ET-1 (Fukuroda, T., et al, "Analysis of Responses to Endothelins in Isolated Porcine Blood Vessels by Using a Novel . . ."). It has previously been reported this vasodilator component is mediated by the ET$_B$ receptor, as indicated by the reported action of selective ET$_B$ agonists in certain tissues (Saeki, T., Ihara, M., Fukuroda, T., Yamagiwa, M., Yano, M. "[Ala1,3,11,15] Endothelin-1 Analogs with ET$_B$ Agonistic Activity," *Biochem. Biophys. Res. Commun.* 179:286, (1991).

Linear tripeptidic compounds are reported as ET$_A$ antagonists (Keiji, H., Masahiro, N., Naoki, F., Masashi, H., Tanaka, H., Kayakiri, N. "Peptides Having Endothelin Antagonist Activity, a Process for the Preparation Thereof and Pharmaceutical Compositions Comprising the Same." EPA 0457 195 A2, May (9, 1991). FR 139317 is a functional antagonist inhibiting the specific binding of [$^{125}$I]ET-1 to porcine and human aortic microsomes in a concentration-dependent, monophasic fashion with IC$_{50}$s of 0.53 and 2.5 nM, respectively. In isolated rabbit aorta, FR 139317 inhibited the ET-1-induced vasoconstriction with a pA$_2$ value of 7.2. An IV administration (bolus) of FR 139317 (1 mg/kg) completely inhibited the pressor response to ET-1, while it had no effect on the initial depressor response, similar to the effects seen with BQ-123 and BQ-153. FR 139317 also suppressed ET-1-induced arrythmia in rats. In a subarachnoid hemorrhage canine model, intracisternal administration of FR 139317 (0.1 mg) significantly inhibited the vasoconstriction of the basilar artery after 7 days (Ihara, M., et al, op.cit.).

We have surprisingly and unexpectedly found that a series of modified amino acids and modified dipeptides and related compounds are receptor antagonists of endothelin. These compounds, their preparation and several methods of using them are known from *J. Med. Chem.* 34:404–414 (1991).

The utilities described in the instant invention are novel and unexpected.

SUMMARY OF THE INVENTION

Elevated levels of endothelin have been postulated to be involved in a number of pathophysiological states including diseases associated with the cardiovascular system as well as various vascular disorders and renal diseases. As antagonists of endothelin, the compounds of Formula I are useful in the treatment of hypertension, myocardial ischemia, congestive heart failure, arrhythmias, angina, pulmonary hypertension, acute and chronic renal failure, atherosclerosis, Buerger's disease, Takayasu's arteritis, Raynaud's phenomenon, pulmonary carcinoma, endocrine disorders, preeclampsia, diabetes, subarachnoid hemorrhage, gastrointestinal diseases, septic shock, and asthma.

The compounds useful in this invention are those of formula

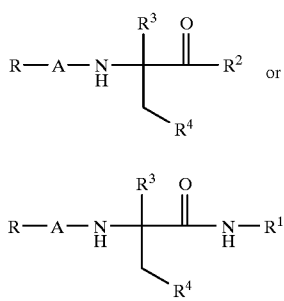

I

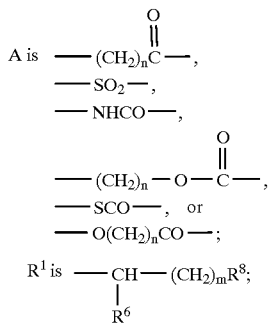

II or a pharmaceutically acceptable salt thereof in unit dosage form wherein:

R is cycloalkyl, cycloalkylalkyl, polycycloalkyl, aryl, heteroaryl, or fluorenylmethyl;

A is
$$-(CH_2)_nC(=O)-,$$
$$-SO_2-,$$
$$-NHCO-,$$
$$-(CH_2)_n-O-C(=O)-,$$
$$-SCO-, \text{ or}$$
$$-O(CH_2)_nCO-;$$

$R^1$ is
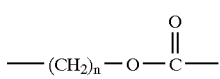

$R^2$ is $NR^5R^6$, —OH or —$NH_2$;
$R^3$ is lower alkyl;
$R^4$ aryl or heteroaryl;
$R^5$ is $(CH_2)_nR^7$; wherein
$R^7$ is aryl or heteroaryl;
R6 is —$(CH_2)_nCO_2H$, —$CONH(CH_2)_nCO_2H$, —$(CH_2)_n$, —$(CH=CH)_nCO_2H$, or —$(CH_2)_nS(CH_2)_nCO_2H$;
$R^8$ is aryl or heteroaryl;
n is an integer of from 0 to 4,
m is an integer from 0 to 4.

DETAILED DESCRIPTION OF THE INVENTION

Compounds useful in the methods of the instant invention are those of Formula I or II wherein
R is adamantyl, cycloalkyl, or cycloalkylmethyl;
A is

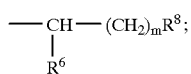

wherein n is 0 or 1;
$R^1$ is

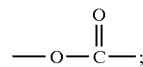

$R^2$ is $NR^5R^6$, —OH or —$NH_2$;
$R^3$ is methyl;
$R^4$ is indole, naphthyl, phenyl, N-alkyl-indole or 2-,3-,4-pyridyl;

$R^5$ is $(CH_2)_nR^7$; wherein
$R^7$ is phenyl or substituted phenyl;
$R^6$ is —$(CH_2)_nCO_2H$, —$CONH(CH_2)_nCO_2H$, —$(CH_2)_n$, —$(CH=CH)_n$, or —$(CH_2)_nS(CH_2)_nCO_2H$; and
$R^8$ is phenyl or substituted phenyl.

More preferred compounds for use in the methods and compositions of the instant invention are those of Formula I or II wherein
R is adamantyl, cycloalkyl, cycloalkylmethyl,
A is $$-O-\overset{O}{\underset{\|}{C}}-;$$

$R^3$ is methyl;
$R^4$ is indole;
$R^5$ is $CH_2CH_2$phenyl; and
$R^6$ is —$CH_2CO_2H$ or —$CH_2CH_2CO_2H$; and
$R^8$ is phenyl or phenyl substituted by —$NH_2$ or —$NO_2$; and
m is 1.

The most preferred compounds of the invention are:

1. (1S-trans)-N-[α-methyl-N-[[(2-methyl-cyclohexyl)-oxy]carbonyl]-D-tryptophyl]-L-3-(phenylmethyl)-β-alanine;

2. [R-(R*,S*)]-[[2-[[3-(1H-indol-3-yl)-2-methyl-1-oxo-2-[[(tricyclo[3.3.1.1$^{3,7}$]dec-2-yloxy)carbonyl]-amino]propyl]amino]-3-phenylpropyl]thio]acetic acid;

3. [R-(R*,S*)]-β-[[3-(1H-indol-3-yl)-2-methyl-1-oxo-2-[[(tricyclo[3.3.1.1$^{3,7}$]dec-2-yloxy)carbonyl]-amino]propyl]amino]benzenebutanoic acid;

4. [S-(R*,R*)]-β-[[3-(1H-indol-3-yl)-2-methyl-1-oxo-2-[[(tricyclo[3.3.1.1$^{3,7}$]dec-2-yloxy)carbonyl]-amino]propyl]amino]benzenebutanoic acid;

5. N-[α-methyl-N-[(tricyclo[3.3.1.1$^{3,7}$]dec-2-yloxy)carbonyl]-D-tryptophyl]-D-3-(phenylmethyl)-β-alanine;

6. [R-[R*,S*-(E)]]-4-[[3-(1H-indol-3-yl)-2-methyl-1-oxo-2-[[(tricyclo[3.3.1.1$^{3,7}$]dec-2-yloxy)carbonyl]-amino]propyl]amino]-5-phenyl-2-pentenoic acid;

7. [R-(R*,S*)]-γ-[[3-(1H-indol-3-yl)-2-methyl-1-oxo-2-[[(tricyclo[3.3.1.1$^{3,7}$]dec-2-yloxy)carbonyl]-amino]propyl]amino]benzenepentanoic acid;

8. (R)-3-[[3-(1H-indol-3-yl) -2-methyl-1-oxo-2-[[(tricyclo[3.3.1.1$^{3,7}$]dec-2-yloxy)carbonyl]amino]-propyl](2-phenylethyl)amino]propanoic acid;

9. L-3-[(4-aminophenyl)methyl]-N-[α-methyl-N-[(tricyclo[3.3.1.1$^{3,7}$]dec-2-yloxy)carbonyl]-D-tryptophyl]-β-alanine;

10. N-[2-methyl-N-[(tricyclo[3.3.1.1$^{3,7}$]dec-2-yloxy)carbonyl]-D-tryptophyl]-L-phenylalanyl-glycine;

11. [R-(R*,S*)]-β-[[3-(1H-indol-3-yl)-2-methyl-1-oxo-2-[[(tricyclo[3.3.1.1$^{3,7}$]dec-2-yloxy)carbonyl]-amino]propyl]amino]-4-nitrobenzenebutanoic acid;

12. N-[α-methyl-N-[(tricyclo[3.3.1.1$^{3,7}$]dec-2-yloxy)carbonyl]-D-tryptophyl]-N-(2-phenylethyl)-glycine;

13. (±)-N-[3-(1H-indol-3-yl)-2-methyl-1-oxo-2-[[(tricyclo[3.3.1.1$^{3,7}$]dec-2-yloxy)carbonyl]amino]-propyl]-N-(2-phenylethyl)glycine;

14. [R-[R*,S*-(E,E)]]-6-[[3-(1H-indol-3-yl)-2-methyl-1-oxo-2-[[(tricyclo[3.3.1.1$^{3,7}$]dec-2-yloxy)-carbonyl]amino]propyl]amino]-7-phenyl-2,4-heptadienoic acid;

15. [R-(R*,S*)]-ε-[[3-(1H-indol-3-yl)-2-methyl-1-oxo-2-[[(tricyclo[3.3.1.1$^{3,7}$]dec-2-yloxy)carbonyl]-amino]propyl]amino]benzeneheptanoic acid; and 16. N-[(cyclohexylamino)carbonyl]-α-methyl-D-tryptophan.

In the compounds of Formula I, the term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The term "and polycycloalkyl cycloalkyl" means a saturated hydrocarbon ring which contains from 3 to 12 carbon atoms, for example, cyclopropyl, cyclobutyl, cyclopentyl, cyclohexyl, adamantyl, and the like.

The term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

The terms "alkoxy" and "thioalkoxy" are O-alkyl or S-alkyl as defined above for alkyl.

The term "aryl" means an aromatic radical which is a phenyl group, a benzyl group, a naphthyl group, a biphenyl group, a pyrenyl group, an anthracenyl group, 3,3-diphenylalanyl, 10,11-dihydro-5H-dibenzo-[a,d]-(cyclohepten-5-yl)glycyl, or a fluorenyl group and the like, unsubstituted or substituted by 1 to 4 substituents selected from alkyl as defined above, alkoxy as defined above, thioalkoxy as defined above, hydroxy, thiol, nitro, halogen, amino,

alkyl wherein alkyl is as defined above,

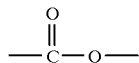

alkyl wherein alkyl is as defined above,

alkyl wherein alkyl is as defined above, or aryl.

The term "arylalkyl" means an aromatic radical attached to an alkyl radical wherein aryl and alkyl are as defined above for example benzyl, fluorenylmethyl and the like.

The term "heteroaryl" means a heteroaromatic radical which is 2-or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino,

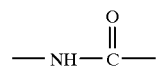

alkyl wherein alkyl is as defined above,

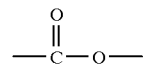

alkyl wherein alkyl is as defined above,

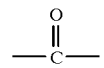

alkyl wherein alkyl is as defined above or phenyl.

The term "heterocycloalkyl" means 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl.

"Halogen" is fluorine, chlorine, bromine or iodine.

The compounds of Formula I are capable of further forming both pharmaceutically acceptable acid addition and/or base salts. All of these forms are within the scope of the present invention.

The synthesis of Compounds 7 and 8 are shown in Schemes 1 and 2.

SCHEME 1

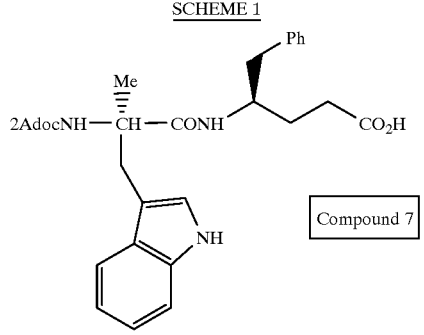

-continued
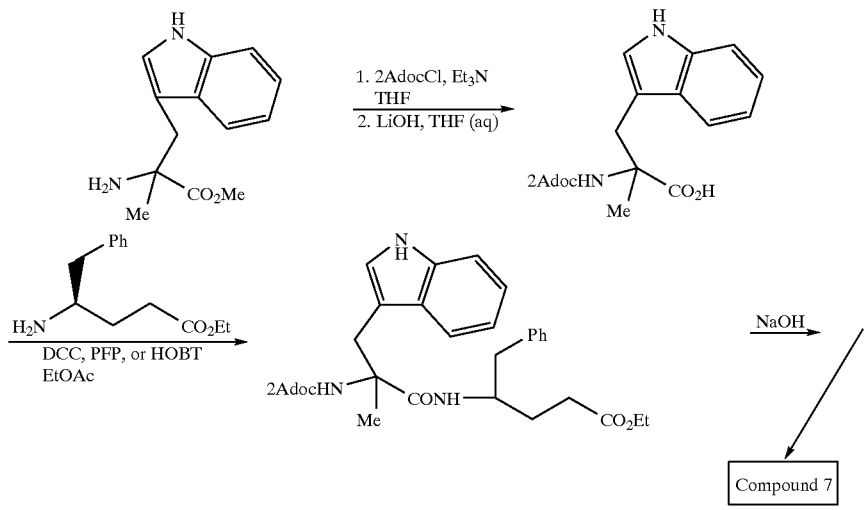
PFP = pentafluorophenol
HOBT = hydrobenzotriazole
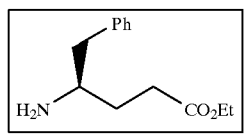
from
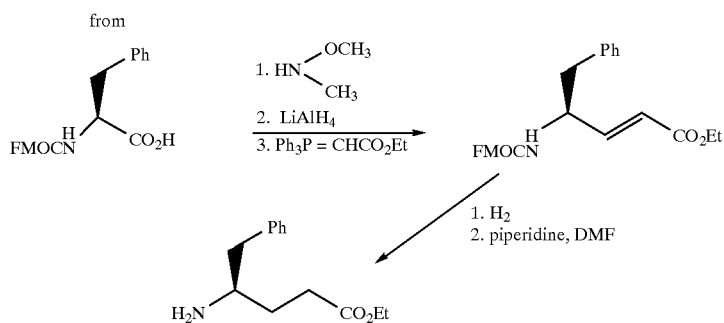
SCHEME 2
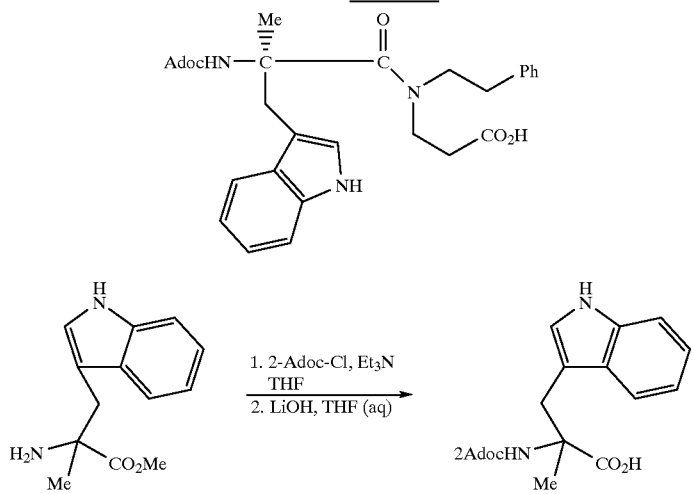

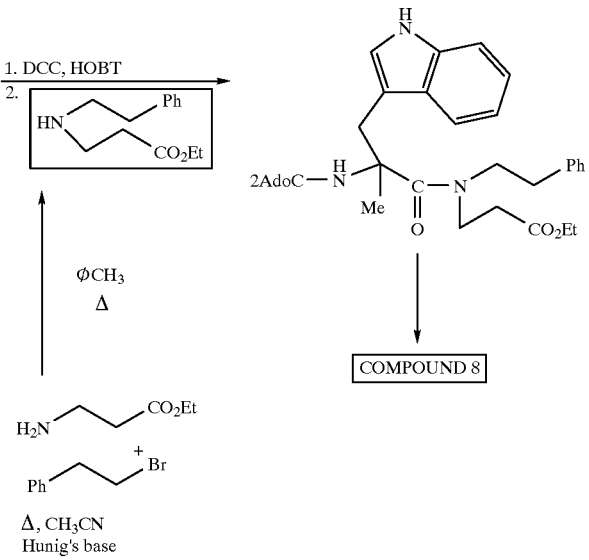

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science* 66:1–19 (1977)).

The acid addition salts of said basic compounds are prepared by contacting the free base form with a sufficient amount of the desired acid to produce the salt in the conventional manner. Preferably a peptide of Formula I can be converted to an acidic salt by treating with an aqueous solution of the desired base, such that the resulting pH is less than 4. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al, "Pharmaceutical Salts," *Journal of Pharmaceutical Science* 66:1–19 (1977)).

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than 9. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of Formula I are valuable antagonists of endothelin. The tests employed indicate that compounds of Formula I possess endothelin antagonist activity. Compounds of Formula I were tested for their ability to inhibit [$^{125}$I]-ET-1([$^{125}$I]-Endothelin-1) binding in a receptor assay according to the following procedures Doherty, A. M., et al, J. Cardiovascul. Pharmacol. 17(Suppl 7):S59–61 (1991) and Doherty, A. M., et al, Bio. Org. Med. Chem. Lett. in press (1992):

ENDOTHELIN RECEPTOR BINDING ASSAY-A (ERBA-A) INTACT CELL BINDING OF [$^{125}$I]-ET-1

Materials and Terms Used:
Cells

The cells used were rabbit renal artery vascular smooth muscle cells grown in a 48-well dish (1 cm$^2$) (confluent cells).

Growth Media

The growth media was Dulbeccos Modified Eagles/Ham's F12 which contained 10% fetal bovine serum and antibiotics (penicillin/streptomycin/fungizone).

Assay Buffer

The assay buffer was a medium 199 containing Hanks salts and 25 mM Hepes buffer (Gibco 380-2350AJ), supplemented with penicillin/streptomycin/fungizone (0.5%) and bovine serum albumin (1 mg/mL).

[$^{125}$I]-ET-1

Amersham radioiodinated endothelin-1 [$^{125}$I]-ET-1 was used at final concentration of 20,000 cpm/0.25 mL (25 pM).

Protocol

First, add 0.5 mL warm assay buffer (described above) to the aspirated growth media and preincubate for 2 to 3 hours in a 37° C. water bath (do not put back in the 5% carbon dioxide). Second, remove the assay buffers, place the dish on ice, and add 150 μL of cold assay buffer described above to each well. Third, add 50 μL each of cold [$^{125}$I]-ET-1 and competing ligand to the solution (at the same time if possible). Next, place dish in a 37° C. water bath for about 2 hours and gently agitate the dish every 15 minutes. Discard the radioactive incubation mixture in the sink and wash wells three times with 1 μL of cold phosphate buffered saline. Last, add 250 mL of 0.25 molar sodium hydroxide, agitate for 1 hour on a rotator, and then transfer the sodium hydroxide extract to gamma counting tubes and count the radioactivity.

ENDOTHELIN RECEPTOR BINDING ASSAY-B (ERBA-B) [$^{125}$I]-ET-1 BINDING IN RAT CEREBELLAR MEMBRANES

Materials and Terms Used:
Tissue Buffer

The tissue is made up of 20 mM tris(hydroxy-methyl) aminomethane hydrochloride (Trizma) buffer, 2 mM ethylenediaminetetra acetate, 100 μM phenylmethylsulfonyl fluoride.

Tissue Preparation

First, thaw one aliquot of frozen rat cerebellar membranes (2 mg protein in 0.5 mL). Next, add 0.5 mL membrane aliquot to 4.5 mL cold tissue buffer, polytron at 7,500 revolutions per minute for 10 seconds. Finally, dilute tissue suspension 1/100 (0.1 mL suspension+9.9 mL tissue buffer), polytron again, and place ice.

Dilution Buffer

Medium 199 with Hank's salts plus 25 mM Hepes+1 mg/mL bovine serum albumin.

[$^{125}$I]-ET-1

Amersham [$^{125}$I]-ET-1 (aliquots of 2×10$^6$ cpm per 100 mL aliquot of [$^{125}$I]-ET-1 with 5.2 mL dilution buffer, place on ice until use (final concentration will be 20,000 cpm per tube, or 25 pM).

Protocol

Add 50 μL each of cold [$^{125}$I]-ET-1 and competing ligand to tubes on ice. Mix in 150 μL of tissue to each tube, vortex briefly, then tap to force all liquids to bottom (total assay volume=250 μL). Then place the tubes in a 37° C. water bath for 2 hours.

Add 2.5 mL cold wash buffer (50 mM Trizma buffer) to each tube, filter, and then wash tube with additional 2.5 mL wash buffer and add to filter. Finally, wash filters with an additional 2.5 mL of cold wash buffer.

Count filters for radioactivity in gamma counter.

AAR Assay for Antagonist Activity

Antagonist activity is measured by the ability of added compounds to reduce endothelin-stimulated arachidonic acid release in cultured vascular smooth muscle cells as arachidonic acid release (AAR). [$^3$H] Arachidonic Acid Loading Media (LM) is DME/F12+0.5% FCS×0.25 mCi/mL [$^3$H] arachidonic acid (Amersham). Confluent monolayers of cultured rabbit renal artery vascular smooth muscle cells were incubated in 0.5 mL of the LM over 18 hours, at 37° C., in 5% CO$_2$. The LM was aspirated and the cells were washed once with the assay buffer (Hank's BSS+10 mM HEPES+fatty acid-free BSA (1 mg/mL), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1 (0.3 nM) and the incubation was extended for 30 minutes. This solution was then collected, 10 μL of scintillation cocktail was added, and the amount of [$^3$H] arachidonic acid was determined in a liquid scintillation counter.

The data in Table I below show the endothelin antagonist activity of representative compounds of Formula I.

TABLE I

Biological Activity of Compounds of Formulas I and II

| Compound Number | Rat Heart IC$_{50}$/μM | Human Placenta IC$_{50}$/μM | ERBA-A IC$_{50}$ (μM) or % inhibition at 10 μM | ERBA-B IC$_{50}$ (μM) | AAR IC$_{50}$ (μM) |
|---|---|---|---|---|---|
| 1 | 9.25 | 0.72 | 46 | 1.5 | (Antag) |
| 2 | 9.06 | 9.88 | | | % inhib at |
| 3 | 7.91 | 0.96 | | | 10 μM |
| 4 | 47.3 | 58.3 | | | 62.4 |
| 5 | 34.5 | 3.84 | | | |
| 6 | | | | 0.87 (IC$_{50}$) | |
| 7 | | | | 0.87 (IC$_{50}$) | |
| 8 | | | 25% at 10 μM | 0.91, 1.8 (IC$_{50}$) | |
| 9 | | | 33.5% | 9.4% | |

TABLE I-continued

Biological Activity of Compounds of Formulas I and II

| Compound Number | Rat Heart $IC_{50}/\mu M$ | Human Placenta $IC_{50}/\mu M$ | ERBA-A $IC_{50}$ ($\mu M$) or % inhibition at 10 $\mu M$ | ERBA-B $IC_{50}$ ($\mu M$) | AAR $IC_{50}$ ($\mu M$) |
|---|---|---|---|---|---|
| 10 | | | 45.0% | 39.7% | |
| 11 | | | 47.7% | 51.4% | |
| 12 | | | 4.1% | 86.0%, 1.8 ($IC_{50}$) | |
| 13 | | | −0.2% | 72.3%, 4.0 ($IC_{50}$) | |
| 14 | | | 54.3% | 39.8% | |
| 15 | | | 51.6% | 36.5% | |
| 16 | | | 1.5 ($IC_{50}$) | >10 ($IC_{50}$) | |

As can ben seen from the data of Table I above, Compounds 6 through 8, 12, and 13 are selective for $ET_B$, while the others are relatively nonselective $ET_A$ and $ET_B$ ligands. In view of the biological activity mediated by both receptor subtypes, the compounds will be useful in a variety of disease states. See Table II below.

TABLE II

Plasma Concentrations of ET-1 in Humans

| Condition | Normal Control | ET Plasma Levels Reported (pg/mL) |
|---|---|---|
| Atherosclerosis | 1.4 | 3.2 (pmol/L) |
| Surgical operation | 1.5 | 7.3 |
| Buerger's disease | 1.6 | 4.8 |
| Takayasu's arteritis | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
| | 0.76 | 4.95 |
| | 0.50 | 3.8 |
| Subarachnoid hemorrhage | 0.4 | 2.2 |
| Crohn's Disease | 0–24 fmol/mg | 4–64 fmol/mg |
| Ulcerative colitis | 0–24 fmol/mg | 20–50 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangio-endothelioma | 4.3 (after removal) | 16.2 |

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 200 mg preferably 0.5 mg to 100 mg according to the particular application and the potency of the active component. The composition can, if desired, also contain other compatible therapeutic agents.

In therapeutic use as antagonist of endothelin, the compounds utilized in the pharmaceutical method of this invention are administered at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

EXAMPLE 1

| Tablet Formulation | |
|---|---|
| | Per/tablet |
| Formula: | |
| Compound 6 | 200.00 µg |
| Citric acid | 1.00 mg |
| Lactose | 25.00 mg |
| Dicalcium phosphate | 25.00 mg |
| Sodium Lauryl Sulfate | 1.00 mg |
| Polyvinylpyrrolidone | 10.00 mg |
| Carbowax 1500 | 5.00 mg |
| 3A alcohol 50 ml/1000 tablets | |
| Corn Starch | 20.00 mg |
| Dry: | |
| Sodium Lauryl Sulfate | 1.00 mg |
| Magnesium stearate | 1.00 mg |

Procedure. Mix together the Compound 6, citric acid, Pluronic F-68, sodium lauryl sulfate, lactose, and dicalcium phosphate. Screen through No. 60 mesh screen. Granulate the screened mix with an alcoholic solution containing the polyvinylpyrrolidone, Carbowax 1500. Add additional alcohol, if necessary, to bring powder mix to a pasty mass. Add corn starch and continue mixing until uniform damp granules are formed. Pass the damp granulation through a No. 10 screen and dry in an oven at 100° C. for about 4 hours. Screen the dried granulation using a No. 16 screen, add sodium lauryl sulfate and magnesium stearate, mix, and compress on a tablet machine to specifications.

Similar tablets are prepared with, for example, Compounds 7 or 8.

EXAMPLE 2

| Capsule Formulation | |
|---|---|
| Formula: | Per/capsule |
| Compound 7 | 100.00 µg |
| Citric acid | 1.00 mg |
| Pluronic F-68 | 1.00 mg |
| Lactose | 100.00 mg |
| Magnesium stearate | 1.00 mg |

Procedure. Mix together the [D-Lys$^9$]ET, citric acid, Pluronic F-68, and lactose. Pass through a No. 80 screen. Add the magnesium stearate, mix, and encapsulate into the proper size gelatin capsule.

Similar capsules are prepared with Compound 8.

EXAMPLE 3

| Parenteral Formulation | |
|---|---|
| R.T.U. solution | |
| Formula per ampoule: | |
| Compound 6 | 200.00 ng |
| Sodium chloride, USP | 9.00 mg |
| Water for injection, USP q.s. to | 1.00 mL |

Procedure. Under stirring and nitrogen bubbling add sodium chloride to about 85% of the prescribed volume of W.F.I. followed by Compound 6. Bring the solution to volume with W.F.I. and sterilize through a sterilizing membrane filter 0.22 µm porosity, collecting the filtrate in sterile area. Fill the filtered solution into sterilized Type I glass ampoules and seal the ampoules by flame.

| Freeze-dried vials. | |
|---|---|
| Formula per vial: | |
| Compound 6 | 200.00 ng |
| Mannitol | 20.00 mg |
| W.F.I.* USP q.s. to | 1.00 mL |

*W.F.I. is removed during freeze drying process.

Procedure. Place about 75% of the foreseen final volume of W.F.I., previously deaerated with nitrogen, into a suitable glass container, then dissolve the prescribed quantity of mannitol. Under stirring and nitrogen bubbling add Compound 6. Sterilize as described for RTU solution, and distribute the filtered solution into sterilized glass vials. The vials are then freeze-dried, stoppered, and sealed.

Parenteral formulations containing compounds of the invention are similarly prepared.

We claim:

1. A method of antagonizing endothelin receptors in a mammal afflicted with elevated levels of endothelin comprising administering to said mammal a therapeutically effective amount of a compound of formula

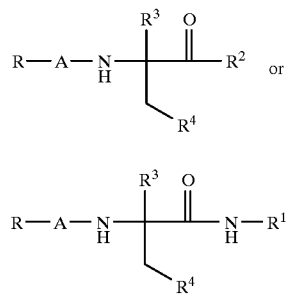 I

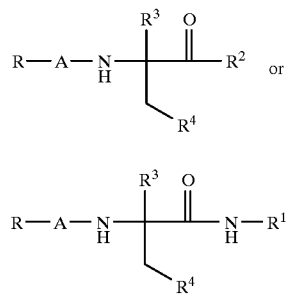 II or a pharmaceutically acceptable salt thereof in unit dosage form wherein:

R is cycloalkyl, cycloalkylalkyl, cycloalkylaryl, polycycloalkyl, aryl, heteroaryl, or fluorenylmethyl;

A is

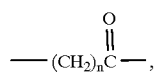

$-SO_2-$, $-NHCO-$,

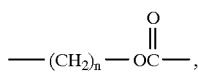

$-SCO-$, or $-O(CH_2)_nCO-$;

$R^1$ is

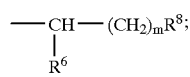

$R^2$ is $NR^5R^6$, $-OH$ or $-NH_2$;

$R^3$ is lower alkyl;

$R^4$ aryl or heteroaryl;

$R^5$ is $-(CH_2)_nR^7$; wherein $R^7$ is aryl or heteroaryl;

$R^6$ is $-(CH_2)_nCO_2H$, $-CONH(CH_2)_nCO_2H$, $-(CH_2)_nCOOH$, $-(CH=CH)_nCOOH$, or $-(CH_2)_nS(CH_2)_nCO_2H$;

$R^8$ is aryl or heteroaryl;

n is an integer of from 0 to 4; and m is an integer of from 1 to 4.

2. A method according to claim 1 wherein

R is adamantyl, cycloalkyl, or cycloalkylmethyl;

A is

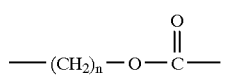

wherein n is 0 or 1;

$R^1$ is

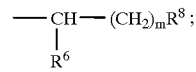

$R^2$ is $NR^5R^6$, $-OH$ or $-NH_2$;

$R^3$ is methyl;

$R^4$ is indole, naphthyl, phenyl, N-alkyl-indole or 2-,3-,4-pyridyl;

$R^5$ is $-(CH_2)_nR^7$; wherein $R^7$ is phenyl or substituted phenyl;

$R^6$ is $-(CH_2)_nCO_2H$, $-CONH(CH_2)_nCO_2H$, $-(CH_2)_nCOOH$, $-(CH=CH)_nCOOH$ or $-(CH_2)_nS(CH_2)_nCO_2H$; and $R^8$ is phenyl or substituted phenyl.

3. A method according to claim 1 wherein R is adamantyl, cycloalkyl, cycloalkylmethyl, A is

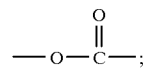

$R^3$ is methyl;

$R^4$ is indole;

$R^5$ is $CH_2CH_2phenyl$;

$R^6$ is $-CH_2CO_2H$ or $-CH_2CH_2CO_2H$; and $R^8$ is phenyl or phenyl substituted by $-NO_2$ or $-NH_2$; and m is 1.

4. A method of treating hypertension comprising administering to a host suffering therefrom a therapeutically effective amount of a compound according to Formula I in unit dosage form.

5. A method of treating congestive heart failure and myocardial infarction comprising administering to a host suffering therefrom a therapeutically effective amount of a compound according to Formula I in unit dosage form.

6. A method of treating septic/endotoxic shock comprising administering to a host suffering therefrom a therapeutically effective amount of a compound according to Formula I in unit dosage form.

7. A method of treating subarachnoid hemorrhage comprising administering to a host suffering therefrom a therapeutically effective amount of a compound according to Formula I in unit dosage form.

8. A method of treating arrhythmias comprising administering to a host suffering therefrom a therapeutically effective amount of a compound according to Formula I in unit dosage form.

9. A method of treating asthma comprising administering to a host suffering therefrom a therapeutically effective amount of a compound according to Formula I in unit dosage form.

10. A method of treating acute or chronic renal failure comprising administering to a host suffering therefrom a therapeutically effective amount of a compound according to Formula I in unit dosage form.

11. A method of treating preeclampsia comprising administering to a host suffering therefrom a therapeutically effective amount of a compound according to Formula I in unit dosage form.

12. A method of treating diabetes comprising administering to a host suffering therefrom a therapeutically effective amount of a compound according to Formula I in unit dosage form.

13. A method of treating neurological disorders comprising administering to a host suffering therefrom a therapeutically effective amount of a compound according to Formula I in unit dosage form.

14. A method of treating pulmonary hypertension comprising administering to a host suffering therefrom a therapeutically effective amount of a compound according to Formula I in unit dosage form.

15. A method of treating congestive heart failure comprising administering to a host suffering therefrom a therapeutically effective amount of [R-[R*,S*-(E)]]-4-[[3-(1H-indol-3-yl)-2-methyl-1-oxo-2-[[(tricyclo[3.3.1.1$^{3,7}$]dec-2-yloxy) carbonyl]-amino]propyl]amino]-5-phenyl-2-pentenoic acid; [R-(R*,S*)]-γ-[[3-(1H-indol-3-yl)-2-methyl-1-oxo-2-[[(tricyclo[3.3.1.1$^{3,7}$] dec-2-yloxy) carbonyl]amino]propyl]amino] benzenepentanoic acid; or (R)-3-[[3-(1H-indol-3-yl)-2-methyl-1-oxo-2-[[(tricyclo [3.3.1.1$^{3,7}$]dec-2-yloxy)carbonyl]-amino]propyl] (2-phenylethyl) amino]propanoic acid; in unit dosage form.

16. A method of treating acute or chronic renal failure comprising administering to a host suffering therefrom a therapeutically effective amount of [R-[R*,S*-(E)]]-4-[[3-(1H-indol-3-yl)-2-methyl-1-oxo-2-[[(tricyclo[3.3.1.1$^{3,7}$] dec-2-yloxy)carbonyl]-amino]propyl]amino]-5-phenyl-2-pentenoic acid; [R-(R*,S*)]-γ-[[3-(1H-indol-3-yl)-2-methyl-1-oxo-2-[[(tricyclo[3.3.1.13,7] dec-2-yloxy) carbonyl]amino]propyl]amino] benzenepentanoic acid; or (R)-3-[[3-(1H-indol-3-yl)-2-methyl-1-oxo-2-[[(tricyclo [3.3.1.1$^{3,7}$]dec-2-yloxy)carbonyl]-amino]propyl] (2-phenylethyl)amino]propanoic acid; in unit dosage form.

* * * * *